United States Patent [19]

Harrison et al.

[11] Patent Number: 4,767,869
[45] Date of Patent: Aug. 30, 1988

[54] PROCESS FOR THE PRODUCTION OF GAMMA-BUTYROLACTONE

[75] Inventors: George E. Harrison, Billericay; Norman Harris, Norton, both of England

[73] Assignee: Davy McKee Limited, London, England

[21] Appl. No.: 80,059

[22] Filed: Jul. 31, 1987

[30] Foreign Application Priority Data

Aug. 1, 1986 [GB] United Kingdom ............... 8618890

[51] Int. Cl.$^4$ ...................... B01D 3/34; C07D 307/02
[52] U.S. Cl. .................................. 549/295; 203/60; 203/74; 203/75; 203/81; 203/82; 203/91
[58] Field of Search ...................... 203/60, 71, 81, 82, 203/91, 74, 75; 549/295; 560/191, 190; 568/864

[56] References Cited

U.S. PATENT DOCUMENTS

| | | | |
|---|---|---|---|
| 2,040,944 | 5/1936 | Lazier | 568/832 |
| 2,079,414 | 5/1937 | Lazier | 568/814 |
| 4,032,583 | 6/1977 | Arganbright et al. | 568/868 |
| 4,584,419 | 4/1986 | Sharif et al. | 568/864 |

FOREIGN PATENT DOCUMENTS

| | | | |
|---|---|---|---|
| 143634 | 5/1985 | European Pat. Off. | |
| 1558895 | 2/1969 | France | |
| 59-27881 | 2/1984 | Japan | 549/295 |
| 62-111976 | 5/1987 | Japan | 549/295 |
| 62-114983 | 5/1987 | Japan | 549/295 |
| 8200118 | 11/1982 | PCT Int'l Appl. | |
| 8500524 | 6/1986 | PCT Int'l Appl. | |
| 8600315 | 12/1986 | PCT Int'l Appl. | |
| 1168220 | 10/1969 | United Kingdom | |
| 2175894 | 12/1986 | United Kingdom | 549/295 |

Primary Examiner—Wilbur Bascomb
Attorney, Agent, or Firm—Bernard, Rothwell & Brown

[57] ABSTRACT

A process is described for the production of substantially pure gamma-butyrolactone from a feed mixture containing a major amount of gamma-butyrolactone and a minor amount of diethyl succinate which comprises fractionally distilling the mixture in a fractionation zone in the presence of added diethyl maleate and recovering from the fractionation zone an overhead vaporous product comprising gamma-butyrolactone which is substantially free from diethyl succinate and a liquid bottom product comprising diethyl maleate and diethyl succinate in admixture one with another. This procedure can be used to separate a gamma-butyrolactone rich fraction obtained by distillation in one or more stages of a crude reaction product obtained by hydrogenation of a C$_4$ dicarboxylic acid ester feedstock that contains a major molar amount of diethyl maleate and a minor molar amount of diethyl succinate, using a diethyl maleate feedstock from an esterification plant to provide both diethyl maleate for use in the fractionation zone and also diethyl maleate for use as feedstock for the hydrogenation process.

20 Claims, 3 Drawing Sheets

PROCESS FOR THE PRODUCTION OF GAMMA-BUTYROLACTONE

This invention relates to a process for the production of gamma-butyrolactone. It also relates to a process for the recovery of gamma-butyrolactone from a mixture containing gamma-butyrolactone and diethyl succinate and possibly also one or more other components.

The production of gamma-butyrolactone and/or butane-1,4-diol by catalytic hydrogenation of dialkyl esters of $C_4$ dicarboxylic acids, such as maleic acid, fumaric acid, succinic acid, and acetylenedicarboxylic acid, has been described on various occasions. In some cases the hydrogenation reaction results in production of tetrahydrofuran as a co-product. Thus Example 12 of U.S. Pat. No. 2,079,414 describes hydrogenation of diethyl succinate at a hydrogen:ester molar ratio of about 10:1 in the vapour phase over a mixed Cd-Cu-Zn chromite catalyst at 367° C. and 2500 p.s.i. (about 173 bar) to yield a mixture of tetramethylene glycol (butane-1,4-diol) and tetrahydrofuran. A similar process is described in Example 1 of U.S. Pat. No. 2,040,944. Moreover WO-A-82/03854 proposes, inter alia, a process for the production of butane-1,4-diol and/or tetrahydrofuran by vapour phase hydrogenation of an dialkyl ester of maleic acid, fumaric acid, acetylenedicarboxylic acid or succinic acid at 75° C. to 300° C. and at a pressure of 0.1 kg/cm² absolute to 100 kg/cm² absolute (about 0.1 bar to about 100 bar) over a catalyst comprising a reduced mixture of copper oxide and zinc oxide.

In EP-A-0143634 and in WO-A-86/03189 there is described a process in which diethyl maleate, diethyl fumarate, diethyl succinate or a mixture of two or more thereof is subjected to catalytic hydrogenation in the vapour phase to yield a reaction product mixture which contains butane-1,4-diol, as well as ethanol and variable amounts of co-products including gamma-butyrolactone, tetrahydrofuran and water, besides minor amounts of diethyl succinate and n-butanol. Although butane-1,4-diol is often the product of primary interest, both gamma-butyrolactone and tetrahydrofuran are sold as commodity chemicals of relatively high value. Hence it is normally desired to recover the co-product gamma-butyrolactone and tetrahydrofuran from the crude reaction mixture as well as the butane-1,4-diol present therein. A related process for the production of gamma-butyrolactone is described in WO-A-86/07358.

When diethyl maleate is used as starting material for the hydrogenation reaction described in EP-A-0143634, WO-A-86/03189 or WO-A-86/07358, the resulting crude reaction mixture may contain, in addition to butane-1,4-diol and gamma-butyrolactone, possibly also a negligible amount of unconverted diethyl maleate, as well as minor amounts of other components including tetrahydrofuran, diethyl succinate, water and n-butanol. The recovery of the desired products, in particular butane-1,4-diol and gamma-butyrolactone, from such mixtures can be difficult since conventional distillation methods may result in production of azeotropic mixtures of other components of the crude reaction mixture with the desired products. Thus although it is a relatively simple matter to separate by distillation at atmospheric pressure tetrahydrofuran and the other relatively low boiling materials, such as water, ethanol and n-butanol, from a crude reaction product mixture obtained by hydrogenation of diethyl maleate and to separate the higher boiling materials into a gamma-butyrolactone rich fraction and into a butane-1,4-diol rich fraction by distillation in one or more stages under reduced pressure, the recovery of pure gamma-butyrolactone from the gamma-butyrolactone rich fraction is problematic because diethyl succinate forms an azeotrope with gamma-butyrolactone and co-distils therewith.

In U.S. Pat. No. 4,032,583 there is described a process for recovering butane-1,4-diol in high purity from a crude reaction mixture which contains, inter alia, gamma-butyrolactone. This process involves adding water and then subjecting the resulting aqueous mixture to solvent extraction with a hydrocarbon solvent followed by distillation of the resulting raffinate. In this way most of the co-products and only a trace of the butane-1,4-diol are extracted into the hydrocarbon solvent, while the aqueous layer contains essentially pure butane-1,4-diol. Before extraction sufficient water is added to produce an aqueous layer preferably containing from about 20 wt % to about 50 wt % water. The water is recovered as an overhead product in the subsequent distillation step and butane-1,4-diol is recovered as a bottom product. As the process involves use of two additional components, namely water and a hydrocarbon solvent, it is somewhat complex to carry out. Moreover as water has a high latent heat of vaporisation and has to be removed in considerable quantity during the distillation step, the process requires considerable energy input for its performance. In addition, although distillation of the hydrocarbon extract phase for solvent recovery is proposed in U.S. Pat. No. 4,032,583, as well as recycle of unconverted ester, no procedure is described for recovery of other potentially useful products from this hydrocarbon extract.

It would be desirable to provide a method of purifying crude gamma-butyrolactone and similar complex mixtures of gamma-butyrolactone and other components including esters, which is simple to operate and has a low energy input requirement. It would also be desirable to provide a method of purifying such materials which enables recovery of all the potentially useful products therefrom. It would further be desirable to provide a process for production of gamma-butyrolactone by hydrogenation of diethyl maleate which overcomes the problems in recovery thereof from the crude reaction product caused by formation of azeotropes with by-product diethyl succinate.

The present invention accordingly seeks to provide a process for the recovery of gamma-butyrolactone from a mixture containing gamma-butyrolactone and diethyl succinate, which is simple in operation and which has a relatively low energy input requirement. It further seeks to provide a process for recovery of gamma-butyrolactone from complex mixtures containing also diethyl succinate, which enables efficient recovery of other useful components of the mixture. It also seeks to provide an improved method for production of gamma-butyrolactone by hydrogenation which obviates the recovery problems associated with formation of azeotropes with by-product diethyl succinate.

According to one aspect of the present invention there is provided a process for the production of substantially pure gamma-butyrolactone from a feed mixture containing a major molar amount of gamma-butyrolactone and a minor molar amount of diethyl succinate which comprises distilling the mixture in a fractionation zone in the presence of added diethyl maleate and recovering from the fractionation zone an overhead vaporous product comprising gamma-butyrolactone which is substantially free from diethyl succinate and a liquid bottom product comprising diethyl maleate and diethyl succinate in admixture one with another.

The invention further provides a process for the production of gamma-butyrolactone which comprises:

(i) hydrogenating a $C_4$ dicarboxylic acid ester feedstock in a hydrogenation zone in the presence of a heterogeneous ester hydrogenation catalyst, said ester feedstock containing a major molar amount of diethyl maleate and a minor molar amount of diethyl succinate;

(ii) recovering from the hydrogenation zone a crude reaction product that is substantially free from diethyl maleate and contains ethanol, butane-1,4-diol, gamma-butyrolactone, and a minor molar amount of diethyl succinate;

(iii) distilling the crude reaction product in one or more stages to yield a gamma-butyrolactone-rich fraction containing, in addition to gamma-butyrolactone, a minor amount of diethyl succinate;

(iv) providing a stream of diethyl maleate;

(v) supplying diethyl maleate of step (iv) and gamma-butyrolactone rich fraction of step (iii) to a fractionation zone;

(vi) fractionally distilling the gamma-butyrolactone rich fraction of step (iii) in the fractionation zone in the presence of said diethyl maleate;

(vii) recovering as an overhead fraction from the fractionation zone a product stream that is substantially free from diethyl succinate and consists essentially of pure gamma-butyrolactone;

(viii) recovering from the fractionation zone a liquid bottom product comprising diethyl maleate and diethyl succinate in admixture one with another; and (ix) recycling material of the liquid bottom product of step (viii) to form at least a part of the $C_4$ dicarboxylic ester feedstock of step (i).

The ester hydrogenation catalyst used in the hydrogenation zone of step (i) can be any solid catalyst that is capable of catalysing the hydrogenation of dialkyl esters of $C_4$ dicarboxylic acids. The ester hydrogenation zone may be operated under liquid phase conditions but is preferably operated under vapour phase conditions. Examples of suitable catalysts include reduced mixtures of copper oxide and zinc oxide of the type disclosed in WO-A-82/03854 and copper chromite catalysts, for example those of the type disclosed in U.S. Pat. No. 2,079,414. In a particularly preferred process the hydrogenation zone is operated under vapour phase conditions using a copper chromite catalyst which contains, before reduction, from about 25 to about 45% by weight of copper and from about 20 to about 35% by weight of chromium. Such vapour phase conditions typically include use of a temperature of from about 150° C. to about 240° C. and a pressure of from about 25 bar to about 75 bar, for example a pressure in the range of from about 35 bar to about 45 bar. The ester hydrogenation zone may comprise two successive hydrogenolysis zones operated according to the teachings of EP-A-0143634, WO-A-86/03189 or WO-A-86/07358.

The crude reaction product from the hydrogenation zone contains as products butane-1,4-diol, gamma-butyrolactone, and tetrahydrofuran. It also contains materials that can be recycled to the hydrogenation zone, such as diethyl succinate, for formation of further product, as well as alkanol (e.g. ethanol) that can be recycled for formation of further diethyl maleate. It also contains as by-products water, n-butanol and "heavies", such as diethyl ethoxy-succinate.

It is not possible to achieve satisfactory separation of such a mixture by fractional distillation because it includes materials which form binary azeotropes with one or more other components of the mixture. In particular gamma-butyrolactone forms a binary azeotrope with diethyl succinate. It has, however, surprisingly been found that distillation of the gamma-butyrolactone rich fraction of step (iii) in the presence of diethyl maleate enables a satisfactory fractional distillation procedure to be adopted.

The fractionation zone may comprise a single fractionation column, in which case a stream of the gamma-butyrolactone rich fraction of step (iii) or other mixture of gamma-butyrolactone and diethyl succinate may be fed to an intermediate part of the fractionation column while diethyl maleate is fed to a part of the distillation column above said intermediate part.

The invention also contemplates a form of plant in which the fractionation zone comprises first and second fractionation columns connected in series, in which a stream of the gamma-butyrolactone rich fraction of step (iii) or other mixture of gamma-butyrolactone and diethyl succinate is fed to an intermediate part of the first fractionation column, in which diethyl maleate is fed to a part of the first fractionation column above said intermediate part, in which a first top fraction is recovered from the top of the first distillation column, said first top fraction being substantially free from diethyl succinate and comprising a mixture of diethyl maleate and gamma-butyrolactone, in which said first top fraction is supplied to the second fractionation column, in which said overhead fractionation comprises the top fraction from the second fractionation column, and in which said liquid bottom product comprises the bottom product from the first fractionation column. Preferably in such a plant a bottom fraction comprising diethyl maleate is recycled from the bottom of the second fractionation column to said first fractionation column.

The fractionation zone is conveniently operated at a pressure in the range of from about 0.01 bar to about 0.75 bar. Throughout this specification and its claims all pressures are expressed in bar absolute, unless otherwise indicated.

The fractional distillation step is carried out in the presence of added diethyl maleate. Desirably the added diethyl maleate is acid free. Such diethyl maleate can be added as substantially pure diethyl maleate. Preferably the diethyl maleate is substantially free from diethyl fumarate, and preferably contains not more than about 0.1 mole % and even more preferably less than about 0.01 mole %, of diethyl fumarate.

Typically the feed mixture to the fractionation zone, e.g. the gamma-butyrolactone rich fraction of step (iii), contains from about 99 mole % to about 75 mole % gamma-butyrolactone and from about 1 mole % to about 25 mole % diethyl succinate.

It will usually be preferred to add diethyl maleate to the distillation zone in a molar ratio with respect to the diethyl succinate in the feed mixture of from about 4:1 to about 200:1.

BRIEF DESCRIPTION OF THE DRAWINGS

In order that the invention may be clearly understood and readily carried into effect three preferred processes for the production of gamma-butyrolactone and three plants designed for operation thereof, will now be described, by way of example only, with reference to the accompanying drawings, FIGS. 1 to 3 of which are each a schematic flow diagram of the plant.

It will be understood by those skilled in the art that, as the drawings are diagrammatic, further items of equipment such as condensers, heat exchangers, reflux drums, column reboilers, pumps, vacuum pumps, temperature sensors, pressure sensors, pressure relief valves, control valves, flow controllers, level controllers, holding tanks, storage tanks, and the like, would additionally be required in a commercial plant. The provision of such additional items of equipment forms no part of the present invention and is in accordance with conventional chemical engineering practice.

DETAILED DESCRIPTION OF THE DRAWINGS

Figure 1:
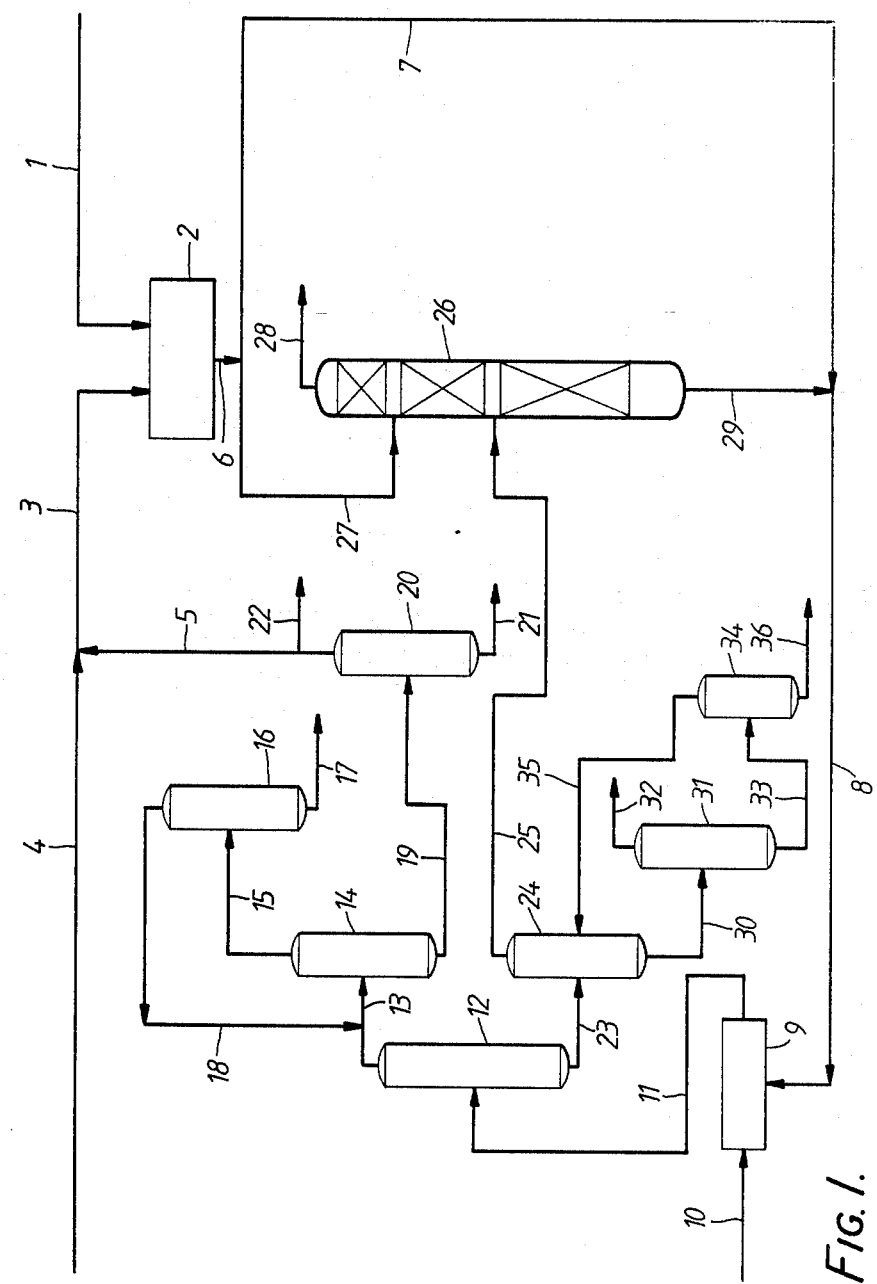

Referring to FIG. 1 of the drawings, maleic anhydride is supplied in line 1 to an esterification plant which is also supplied in line 3 with a mixture of makeup 2 ethanol from line 4 and of recycled ethanol from line 5. Esterification plant produces a stream of acid free diethyl maleate in line 6, part of which is fed by way of lines 7 and 8 to a vapour phase catalytic hydrogenation plant 9 which is also fed with hydrogen in line 10. In plant 9 the diethyl maleate is hydrogenated in the presence of excess gaseous hydrogen by passage, in the vapour phase, over a copper chromite catalyst to produce a crude product stream in line 11 that is substantially free from diethyl maleate and contains, as products, a mixture of butane-1,4-diol, gamma-butyrolactone, and tetrahydrofuran, and, as recyclable materials, diethyl succinate, and ethanol, as well as minor amounts of byproducts, including water, n-butanol, and "heavies" such as diethyl ethoxysuccinate.

Esterification plant 2 may include a noncatalytic monoesterification stage, in which maleic anhydride is reacted with excess ethanol to yield monoethyl maleate according to the following equation:

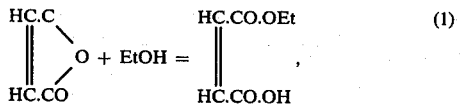

and one or more catalytic esterification stages, in which the resulting monoethyl maleate is further reacted with ethanol to yield diethyl maleate, according to the following equation:

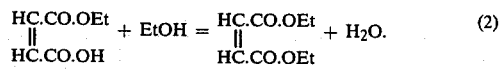

Although homogeneous liquid phase esterification catalysts, such as sulphuric acid, can be used, it is preferred to use in the catalytic esterification stage or stages a heterogeneous solid catalyst, such as an ion exchange resin containing sulphonic acid groups, for example Amberlyst 16. (The word "Amberlyst" is a trade mark). This obviates the need to neutralise the catalyst as is necessary when using a homogeneous catalyst, such as sulphuric acid. Hence the production of significant quantities of waste liquors and loss of potential product, in the form of monoethyl maleate, therein is avoided by use of a heterogeneous catalyst. As equation (2) is reversible, as much water of esterification as possible must be removed if the yield of diethyl maleate is to be maximised.

In one scheme monoethyl maleate is passed in co-current with excess ethanol through a primary esterification reactor containing a charge of a suitable ion exchange resin (e.g. Amberlyst 16), the resulting intermediate reaction mixture is distilled to remove excess ethanol and water therefrom, and then the bottom product containing a mixture of mono- and diethyl maleates is fed in countercurrent to dry ethanol through one or more further esterification stages, each also containing a charge of a resin catalyst (e.g. Amberlyst 16). Further details of such a plant can be found in copending European patent application No. 87306805.0 filed simultaneously herewith.

Final traces of monoethyl maleate and any other acid material present can be removed from the system by a two stage distillation procedure according to the teachings of copending European patent application No. 87306807.6 filed simultaneously herewith, possibly followed by the washing procedure taught in copending British patent application No. 8618893 filed Aug. 1, 1986. In this two stage distillation procedure monoethyl maleate is allowed to decompose thermally in the first distillation stage to yield ethanol, which is removed overhead, and maleic anhydride, which co-distils with product diethyl maleate and is separated therefrom in a second distillation stage. Further distillation stages can be used to remove the final traces of acid materials therefrom. The alternative washing procedure involves washing the ester with an alkaline solution of disodium maleate containing an alkali metal hydroxide, carbonate, bicarbonate or a mixture thereof, followed by distillation to remove traces of water and sodium ions.

In an alternative arrangement described in European patent application No. 87306805.0 filed simultaneously herewith, and in copending International patent application No. PCT/GB 87/00547 filed simultaneously, a primary esterification reactor is used that contains a charge of Amberlyst 16 resin, or similar solid catalyst. The resulting mixture of diethyl maleate, monoethyl maleate, ethanol and water is distilled to remove substantially all the ethanol and water therefrom, and the ester mixture (typically containing an approximately 65:35 molar mixture of diethyl and monoethyl maleates) is reacted with further ethanol in a continuously stirred tank reactor containing also a charge of Amberlyst 16 resin or other solid catalyst from which a stream containing an approximately 85:15 molar mixture of diethyl and monoethyl maleates, water and ethanol is recovered. This is then distilled to remove substantially all water and ethanol therefrom and the residue is subjected to the procedures of copending European patent application No. 87306807.6 filed simultaneously herewith, and possibly also to the procedure of copending British patent application No. 8618893 filed Aug. 1, 1986.

Hydrogenation plant 9 may include a single catalytic zone or may include two hydrogenolysis zones operated according to the teachings of EP-A-0143634, WO-A86/03189 or WO-A-86/07358.

The crude hydrogenation product is fed in line 11 to a first distillation column 12, which is operated under vacuum at a pressure of 0.27 bar with a head temperature of 48° C. The "light ends", i.e. a mixture of tetrahydrofuran, ethanol, water, and n-butanol, are stripped off in column 12, recovered overhead in line 13, and passed to a second distillation column 14. Column 14 is operated at 1.2 bar at a head temperature of 58° C. A first tetrahydrofuran/water azeotrope is recovered overhead in line 15 and is passed to a third distillation column 16 which is operated at 7.0 bar with a head temperature of 126° C. Essentially pure tetrahydrofuran is recovered as a bottom product from third distillation column 16 in line 17. The overhead product in line 18 from third distillation column 16 is a second tetrahydrofuran/water azeotrope which is markedly richer in water than the first tetrahydrofuran/water azeotrope from the second column 14. This second azeotrope is recycled from line 18 by way of line 13 to second column 14.

The bottom product in line 19 from second column 14 is a wet mixture of ethanol and n-butanol. This is fed to a fourth distillation column 20 which is operated at 1.2 bar with a head temperature of 85° C. The overhead product in line 5 from this column is a slightly wet ethanol which is recycled to esterification plant 2. The bottom product in line 21 from column 20 is dry n-butanol. Line 22 represents an ethanol purge line.

It will thus be seen that separation of the "light ends" mixture of tetrahydrofuran, ethanol, water, and n-butanol from first distillation column 12 can be achieved in the three further distillation columns 14, 16 and 20, operating at 1.2 bar, 7.0 bar and 1.2 bar respectively.

The "heavy ends" fraction in line 23 from first distillation column 12 is a mixture containing, in addition to butane-1,4-diol and gamma-butyrolactone, a minor amount of diethyl succinate, as well as a minor amount of "heavies", such as diethyl ethoxysuccinate. This is fed to a fifth distillation column 24, which is operated under vacuum at a pressure of 0.12 bar with a head temperature of 134° C. The overhead product from column 24 is a mixture of diethyl succinate, gamma-butyrolactone and a minor amount of butane-1,4-diol; this is passed by way of line 25 to a sixth distillation column 26 which is operated at a pressure of 0.067 bar and at a head temperature of approximately 128° C. Column 26 is supplied by way of line 27, at a point above the point of connection of line 25, with diethyl maleate from line 6. Hence the mixture of gamma-butyrolactone, diethyl succinate, and butane-1,4-diol in line 25 is distilled in sixth column 26 in the presence of diethyl maleate. The overhead product in line 28 from column 26 is substantially pure gamma-butyrolactone. The bottom product from column 26 comprises a mixture of diethyl succinate and diethyl maleate and possibly a trace amount of "heavies"; this is taken by way of line 29 and admixed with diethyl maleate in line 7 to form the stream in line 8. Hence the diethyl succinate and diethyl maleate are recycled to the hydrogenation plant 9.

Reverting to fifth column 24, the bottom product therefrom in line 30 is a mixture of butane-1,4-diol and "heavies". This is distilled in seventh distillation column 31 at a pressure of 0.24 bar and a head temperature of 134° C. to give an overhead product, which is substantially pure butane-1,4-diol, in line 32 and a bottom "heavies" product in line 33. This "heavies" product is stripped in column 34 of remaining traces of butane-1,4-diol, which are recycled to fifth column 24 in line 35. The stripped "heavies" stream in line 36 is exported beyond battery limits or is used as boiler fuel in the plant.

Figure 2:
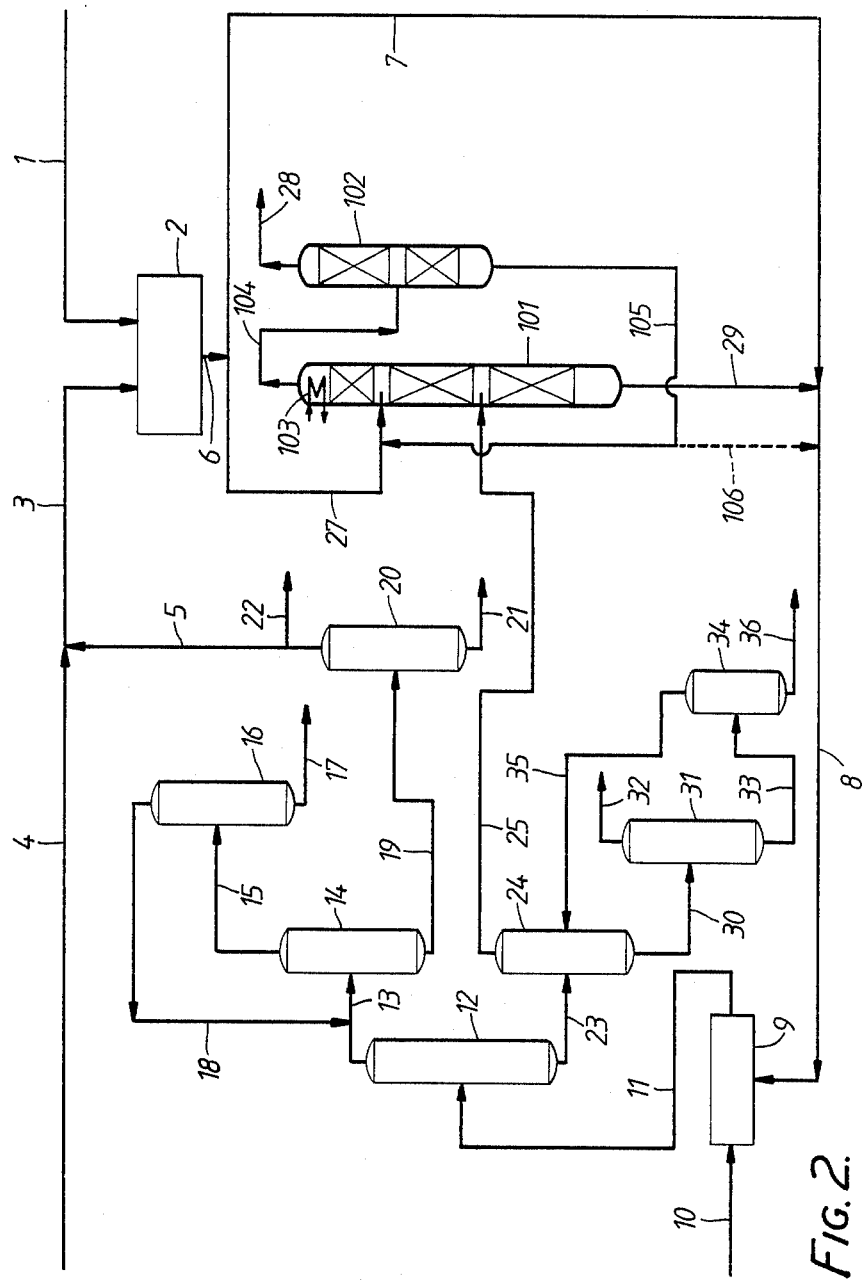

The plant of FIG. 2 is generally similar to that of FIG. 1 and the same reference numerals have been used therein to refer to the same items of equipment that are found in the plant of FIG. 1.

In the plant of FIG. 2 sixth column 26 is replaced by a pair of columns 101 and 102. As in the case of column 26 of the plant of FIG. 1, diethyl maleate is supplied at a temperature of 40° C. to column 101 in line 27 at a point above the connection of line 25. Column 101 is operated at a head pressure of 0.12 bar and at a head temperature of 134° C. Condenser 103 ensures provision of a reflux stream for column 101. The vaporous stream in line 104 is substantially free from diethyl succinate but is predominantly a mixture of gamma-butyrolactone and diethyl maleate. The bottom product in line 29 is a mixture of gamma-butyrolactone and diethyl succinate.

Column 102 is operated at a head pressure of 0.067 bar. The head temperature is 117° C. The overhead fraction in line 28 is substantially pure gamma-butyrolactone, whilst the bottom product in line 105, which is mainly diethyl maleate, but contains also a minor amount of gamma-butyrolactone, is recycled at 140° C. to line 27 and column 101.

In the plant of FIG. 2 the danger of carry over of diethyl succinate is reduced, compared with the plant of FIG. 1. Thus, if for any reason the output from esterification plant 2 should be interrupted so that no diethyl maleate is temporarily available in line 6 for supply to line 27, then diethyl maleate can be recycled between columns 101 and 102 in lines 104 and 105, thus ensuring that diethyl succinate appears in the bottom product in line 29 from column 101 and not in the overhead product in line 104 until either columns 101 and 102 can be shut down or else the supply of diethyl maleate in line 6 can be restored.

Reference numeral 106 indicates a line by means of which some or all of the bottom product in line 105 can be recycled to the hydrogenation plant 9 instead of being recycled to column 101.

The plant of FIG. 2 is particularly suited for use in cases where hydrogenation plant 9 is operated according to the teachings of WO-A-86/07358, such that gamma-butyrolactone, rather than butane-1,4-diol, is the major $C_4$ product in the crude hydrogenation mixture in line 11, since in this case the requirement for diethyl maleate in columns 101 and 102 may exceed the rate of supply thereof in line 6. In this case there would be some danger, in the plant of FIG. 1, of diethyl succinate appearing in the overhead vaporous product from column 26 in line 28.

As described above, part of the diethyl maleate in line 6 of the plants of FIGS. 1 and 2 flows to hydrogenation plant 9 in lines 7 and 8 whilst the remainder flows in line 27 to column 26 or to first column 101. If desired, or if more convenient or expedient, line 7 can be omitted so that all of the diethyl maleate from line 6 passes by way of line 27 to the column 26 or to columns 101 and 102 and then by way of lines 29 and 8 to the hydrogenation zone 9.

Figure 3:
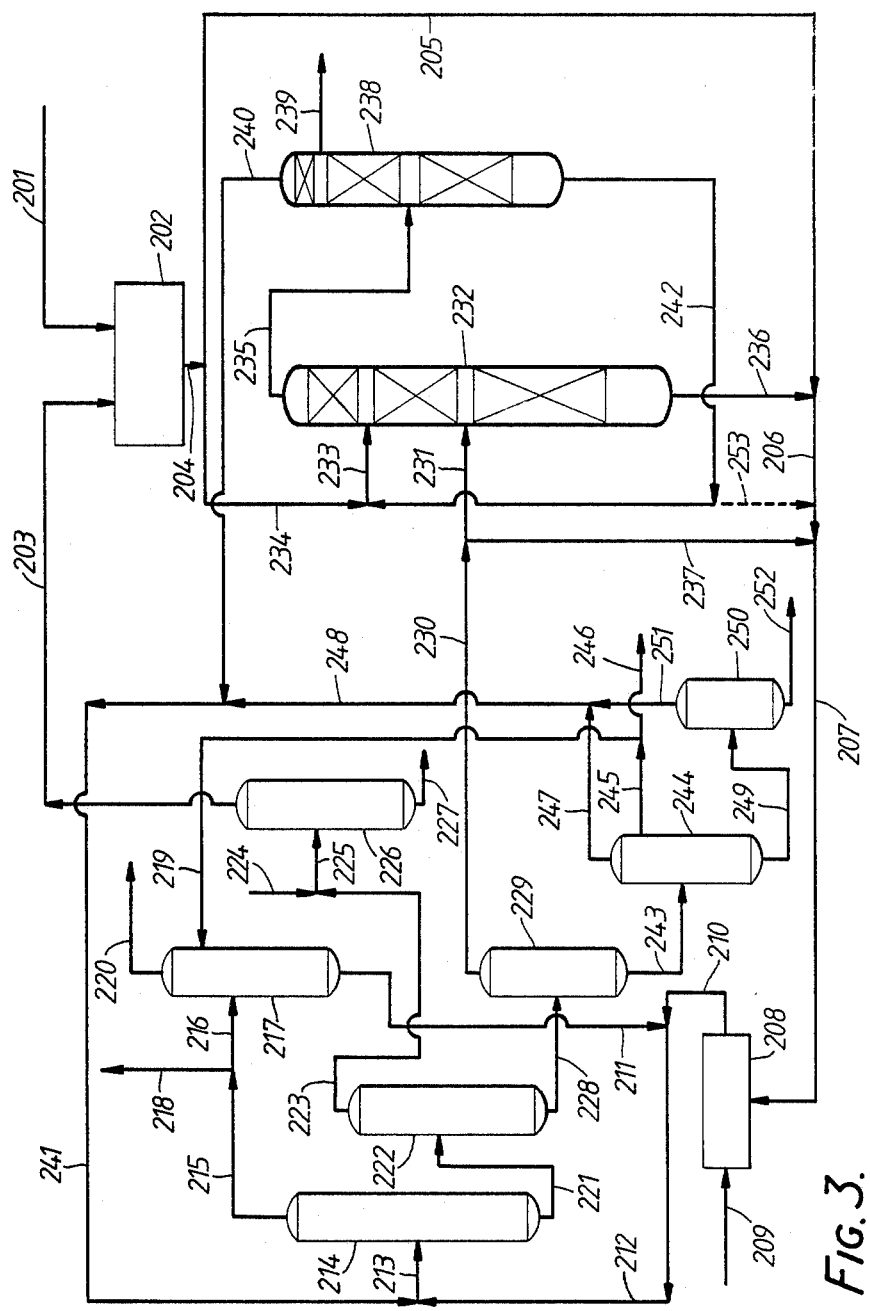

Referring to FIG. 3 of the drawings, maleic anhydride is supplied in line 201 to an esterification plant 202 which is also supplied in line 203 with ethanol. Esterification plant 202 is generally similar to plant 2 of FIGS. 1 and 2 and produces a stream of acid-free diethyl maleate in line 204, part of which is fed by way of lines 205, 206 and 207 to a vapour phase catalytic hydrogenation plant 208 which is also fed with hydrogen in line 209 and is generally similar to plant 8. The crude hydrogenation product in line 210 is admixed with recycled material in line 211 and is fed by way of lines 212 and 213 to a first distillation column 214 which is operated at a pressure of 1.1 bar and at a head temperature of 66.1° C. A mixture of tetrahydrofuran, ethanol and water is recovered overhead in line 215, together with any hydrogen dissolved in the crude product in line 210. This mixture is condensed in a condenser (not shown) before being passed in line 216 to a second distillation column 217. A vent gas stream consisting mainly of hydrogen is taken in line 218 for use as a fuel or for venting to a flare stack. Column 217 is operated at 1.1 bar and with a head temperature of 68.3° C. A stream of butane-1,4-diol is fed to an upper part of second distillation column 217 in line 219 at a mass flow rate which is approximately 6 to 7 times that of the mass flow rate in line 216 so as to give a butane-1,4-diol:tetrahydrofuran molar ratio of approximately 4.5:1 in second distillation column 217. Essentially pure tetrahydrofuran is recovered as an overhead product from second distillation column 217 in line 220.

The bottom product in line 211 from second distillation column 217 is a wet mixture of tetrahydrofuran, ethanol, and a minor amount of n-butanol, dissolved in butane-1,4-diol. This is recycled to the first distillation column 214, after admixture with crude product in line 210, by means of lines 212 and 213.

The bottom fraction from first distillation column 214 contains, in addition to the high boiling materials present, such as butane-1,4-diol, gamma-butyrolactone, diethyl succinate, and a minor amount of diethyl ethoxysuccinate and other "heavies", also ethanol, water, and n-butanol, but only a trace amount of tetrahydrofuran. This bottom fraction is passed in line 221 to a third distillation column 222 which is operated at a pressure of 0.26 bar. Low boiling materials, i.e. remaining traces of tetrahydrofuran, water, ethanol and n-butanol are recovered overhead in line 223 at a head temperature of 47.8° C. and are mixed with make-up ethanol supplied in line 224. The resulting mixed stream is supplied in line 225 to a fourth distillation column 226. Column 226 is operated at 2 bar and at a head temperature of 96.7° C. A wet ethanol stream is recovered overhead in line 203 for use in the esterification plant 202. Esterification plant 202 includes a water recovery section (not shown) whereby the water mass balance of the plant can be maintained.

The bottom product from fourth distillation column 226, which is recovered in line 227, is substantially pure n-butanol.

The "heavy ends" fraction in line 228 from third distillation column 222 is a mixture containing, in addition to butane-1,4-diol and gamma-butyrolactone, a minor amount of diethyl succinate, as well as a minor amount of "heavies", such as diethyl ethoxysuccinate. This is fed to a fifth distillation column 229 which is operated under vacuum at a pressure of 0.13 bar with a head temperature of 136° C. The overhead product from column 229 is a mixture of diethyl succinate, gamma-butyrolactone and a minor amount of butane-1,4-diol; this is passed by way of lines 230 and 231 to a sixth distillation column 232 which is operated at a pressure of 0.13 bar and at a head temperature of approximately 141° C. Column 232 is also supplied by way of line 233, at a point above the point of connection of line 231, with diethyl maleate from line 204 via line 234. Hence the mixture of gamma-butyrolactone, diethyl succinate and butane-1,4-diol in line 231 is distilled in sixth column 232 in the presence of diethyl maleate. The overhead product in line 235 from column 232 is a mixture of diethyl maleate and gamma-butyrolactone. The bottom product from column 232 comprises a mixture of diethyl succinate and diethyl maleate, and possibly a trace amount of "heavies"; this is taken by way of line 236 and admixed with diethyl maleate in line 205 to form the stream in line 206. Hence the diethyl succinate and diethyl maleate recovered from the bottom of column 232 are recycled to the hydrogenation plant 208 by way of lines 206 and 207.

If desired some of the material in line 230 can be recycled to the hydrogenation plant 208 by way of lines 237 and 207.

As already mentioned, the stream in line 235 is substantially free from diethyl succinate and consists predominantly of a mixture of gamma-butyrolactone and diethyl maleate. This is passed to a seventh distillation column 238 which is operated at a pressure of 0.13 bar and at a head temperature of 135° C. A side stream is taken from near the top of column 238 in line 239. This stream consists essentially of gamma-butyrolactone. A purge stream can be taken in line 240 for recycle of any "lights" which reach column 238 to first distillation column 214; this purge stream is recycled from line 240 by way of line 241.

The bottom product from column 238 is mainly diethyl maleate but contains also a minor amount of gamma-butyrolactone. This is recycled to sixth distillation column 232 by way of lines 242 and 233.

Although columns 232 and 238 could be combined into a single column, it is preferred to utilise two columns 232 and 238 so as to reduce the danger of carry-over of diethyl succinate. Thus, if for any reason, the output from esterification plant 202 should be interrupted so that no diethyl maleate is temporarily available in line 204 for supply to line 234, then diethyl maleate can be recycled between columns 232 and 238 by way of lines 242 and 233, thus ensuring that diethyl succinate appears in the bottom product in line 236 from column 232 and not in the gamma-butyrolactone product in line 239, until either columns 232 and 238 can be shut down or else the supply of diethyl maleate in line 204 can be restored.

As described above, part of the diethyl maleate in line 204 of the plant of the drawing flows to hydrogenation plant 208 in lines 205, 206 and 207, whilst the remainder flows in lines 234 and 233 to column 232. If desired, or if more convenient or expedient, line 205 can be omitted so that all of the diethyl maleate from line 204 passes by way of lines 234 and 233 to column 232 and thence by way of lines 236, 206 and 207 to the hydrogenation plant 208.

Reverting to fifth column 229, the bottom product therefrom in line 243 is a mixture of butane-1,4-diol and "heavies". This is distilled in eighth distillation column 244 which is operated at a pressure of 0.1 bar and at a head temperature of 262.2° C. A stream of substantially pure butane-1,4-diol is recovered from near the top of column 244 in line 245. Part of this is passed to second distillation column 217 in line 219, whilst the remainder is passed on as product butane-1,4-diol in line 246. A bleed stream may be taken from the reflux stream for column 244 in line 247 and recycled to first distillation column 214 by way of lines 248 and 241 for the purpose of recycling any "lights" which may reach column 244.

The bottom product from distillation column 244 contains butane-1,4-diol and "heavies", such as diethyl ethoxysuccinate. This stream in line 249 is passed to a further distillation column 250 which is operated at a head temperature of 165° C. and at a pressure of 0.1 bar. The overhead product in line 251 is combined with overhead product in line 247 and passed by way of lines 248, 241 and 113 to first distillation column 214. A bottom product stream consisting mainly of diethyl ethoxysuccinate and other "heavies" in line 252 can be exported beyond site limits or can be used as boiler fuel in the plant.

Reference numeral 253 indicates a line whereby some or all of the bottom product in line 242 can be recycled to the hydrogenation plant 208 instead of being recycled to column 232 via line 233.

What is claimed is:

1. A process for the production of substantially pure gamma-butyrolactone from a feed mixture containing a major molar amount of gamma-butyrolactone and a minor molar amount of diethyl succinate which comprises fractionally distilling the mixture in a fractionation zone in the presence of added diethyl maleate and recovering from the fractionation zone an overhead vaporous product comprising gamma-butyrolactone which is substantially free from diethyl succinate and a liquid bottom product comprising diethyl maleate and diethyl succinate in admixture one with another.

2. A process according to claim 1, in which the fractionation zone comprises a single fractionation column, in which a stream of the mixture is fed to an intermediate part of the fractionation column and in which diethyl maleate is fed to a part of the distillation column above said intermediate part.

3. A process according to claim 1, in which the fractionation zone comprises first and second fractionation columns connected in series, in which a stream of the mixture is fed to an intermediate part of the first fractionation column, in which diethyl maleate is fed to a part of the first fractionation column above said intermediate part, in which a first top fraction is recovered from the top of the first distillation column, said first top fraction being substantially free from diethyl succinate and comprising a mixture of diethyl maleate and gamma-butyrolactone, in which said first top fraction is supplied to the second fractionation column, in which said overhead fraction comprises the top fraction from the second fractionation column, and in which said liquid bottom product comprises the bottom product from the first fractionation column.

4. A process according to claim 3, in which a bottom fraction comprising diethyl maleate is recycled from the bottom of the second fractionation column to said first fractionation column.

5. A process according to claim 1, in which the fractionation zone is operated at a pressure in the range of from about 0.01 bar to about 0.75 bar.

6. A process according to claim 1, in which the diethyl maleate is added in the form of an acid free stream of diethyl maleate.

7. A process according to claim 1, in which the diethyl maleate is added in the form of a stream of diethyl maleate that is substantially free from diethyl fumarate.

8. A process according to claim 1, in which the feed mixture contains from about 99 mole % to about 75 mole % gamma-butyrolactone and from about 1 mole % to about 25 mole % diethyl succinate.

9. A process according to claim 1, in which diethyl maleate is added to the distillation zone in a molar ratio with respect to the diethyl succinate in the feed mixture of from about 4:1 to about 200:1.

10. A process for the production of gamma-butyrolactone which comprises:
(i) hydrogenating a $C_4$ dicarboxylic acid ester feedstock in a hydrogenation zone in the presence of a heterogeneous ester hydrogenation catalyst, said ester feedstock containing a major molar amount of diethyl maleate and a minor molar amount of diethyl succinate;
(ii) recovering from the hydrogenation zone a crude reaction product that is substantially free from diethyl maleate and contains ethanol, butane-1,4-diol, gamma-butyrolactone, and a minor amount of diethyl succinate;
(iii) distilling the crude reaction product in one or more stages to yield a gamma-butyrolactone-rich fraction containing, in addition to gamma-butyrolactone, a minor amount of diethyl succinate; and
(iv) fractionally distilling the gamma-butyrolactone-rich fraction mixture in a fractionation zone in the presence of added diethyl maleate and recovering from the fractionation zone an overhead vaporous product comprising gamma-butyrolactone which is substantially free from diethyl succinate and a liquid bottom product comprising diethyl maleate and diethyl succinate.

11. A process according to claim 10, in which the fractionation zone comprises a single fractionation column, in which the gamma-butyrolactone rich fraction is fed to an intermediate part of the fractionation column and in which diethyl maleate is fed to a part of the distillation column above said intermediate part.

12. A process according to claim 10, in which the fractionation zone comprises first and second fractionation columns connected in series, in which the gamma-butyrolactone rich fraction is fed to an intermediate part of the first fractionation column, in which diethyl maleate is fed to a part of the first fractionation column above said intermediate part, in which a first top fraction is recovered from the top of the first distillation column, said first top fraction being substantially free from diethyl succinate and comprising a mixture of diethyl maleate and gamma-butyrolactone, in which said first top fraction is supplied to the second fractionation column, in which said overhead fraction comprises the top fraction from the second fractionation column, and in which said liquid bottom product comprises the bottom product from the first fractionation column.

13. A process according to claim 12, in which a bottom fraction comprising diethyl maleate is recycled from the bottom of the second fractionation column to said first fractionation column.

14. A process according to claim 10, in which the fractionation zone is operated at a pressure in the range of from about 0.01 bar to about 0.75 bar.

15. A process according to claim 10, in which the added diethyl maleate of step (iv) is substantially free from diethyl fumarate.

16. A process according to claim 10, in which the gamma-butyrolactone rich fraction contains from about 99 mole % to about 75 mole % gamma-butyrolactone and from about 1 mole % to about 25 mole % diethyl succinate.

17. A process according to claim 10, in which diethyl maleate is added to the distillation zone in a molar ratio with respect to the diethyl succinate in the gamma-butyrolactone rich fraction of from about 4:1 to about 200:1.

18. A process according to claim 10, in which step (iii) includes recovery of an ethanol containing fraction which is used for reaction with maleic anhydride to produce further diethyl maleate for use in the process.

19. A process according to claim 10, in which the added diethyl maleate of step (iv) is acid free.

20. A process as claimed in claim 10, wherein the liquid bottom product of step (iv) is recycled to form at least a part of the $C_4$ dicarboxylic ester feedstock of step (i).

* * * * *